(12) United States Patent
Green et al.

(10) Patent No.: US 6,313,362 B1
(45) Date of Patent: Nov. 6, 2001

(54) AROMATIC ALKYLATION PROCESS

(75) Inventors: John R. Green, Yardley, PA (US); Thomas F. Degnan, Moorestown, NJ (US); Yun-Yang Huang, Voorhees, NJ (US); Chaya R. Venkat, Princeton, NJ (US); Ronald A. Weiss, Flemington, NJ (US)

(73) Assignee: ExxonMobil Corporation, Fairfax, VA (US)

( * ) Notice: Subject to any disclaimer, the term of this patent is extended or adjusted under 35 U.S.C. 154(b) by 0 days.

(21) Appl. No.: 09/213,798

(22) Filed: Dec. 17, 1998

(51) Int. Cl.[7] .............. C07C 2/64; C07C 6/00; C07C 7/00
(52) U.S. Cl. ............ 585/323; 585/319; 585/820; 585/823; 585/824
(58) Field of Search .................. 585/319, 323, 585/820, 823, 824

(56) References Cited

U.S. PATENT DOCUMENTS

| | | | |
|---|---|---|---|
| 2,778,863 | 1/1957 | Maisel et al. | 260/674 |
| 3,400,169 | 9/1968 | Eng et al. | 260/674 |
| 3,835,037 | 9/1974 | Fairweather et al. | 208/260 |
| 3,888,939 | 6/1975 | Rosback | 260/677 |
| 4,008,289 * | 2/1977 | Ward et al. | 585/448 |
| 4,008,290 | 2/1977 | Ward | 260/672 |
| 4,309,281 | 1/1982 | Dessau | 208/310 Z |
| 4,459,426 * | 7/1984 | Inwood et al. | 585/323 |
| 4,501,652 | 2/1985 | Le et al. | 208/57 |
| 4,774,377 * | 9/1988 | Barger et al. | 585/323 |
| 4,795,550 | 1/1989 | Sachtler et al. | 208/307 |
| 4,857,666 * | 8/1989 | Barger et al. | 585/323 |
| 4,870,222 * | 9/1989 | Bakas et al. | 585/323 |
| 4,891,458 | 1/1990 | Innes et al. | 585/323 |
| 4,954,663 | 9/1990 | Marler et al. | 568/791 |
| 4,962,256 | 10/1990 | Le et al. | 585/467 |
| 4,992,606 | 2/1991 | Kushnerick et al. | 585/467 |
| 5,001,295 | 3/1991 | Angevine et al. | 585/467 |
| 5,043,501 | 8/1991 | Del Rossi et al. | 585/323 |
| 5,243,116 | 9/1993 | Lee et al. | 585/467 |
| 5,744,686 | 4/1998 | Gajda | 585/823 |
| 5,847,253 | 12/1998 | Ho et al. | 585/450 |

FOREIGN PATENT DOCUMENTS

WO98/07673   2/1998   (WO).

\* cited by examiner

*Primary Examiner*—Walter D. Griffin

(57) ABSTRACT

Akylation product is contacted with a purification medium in a liquid phase pre-reaction step to remove impurities and form a purified stream. The purified stream may then be further processed by liquid phase transalkylation to convert the polyalkylated aromatic compound to a monoalkylated aromatic compound. The process may use a large pore molecular sieve catalyst such as MCM-22 as the purification medium in the pre-reaction step because of its high reactivity for alkylation, strong retention of catalyst poisons and low reactivity for oligomerization under the pre-reactor conditions. Olefins, diolefins, styrene, oxygenated organic compounds, sulfur containing compounds, nitrogen containing compounds and oligomeric compounds are removed.

9 Claims, 1 Drawing Sheet

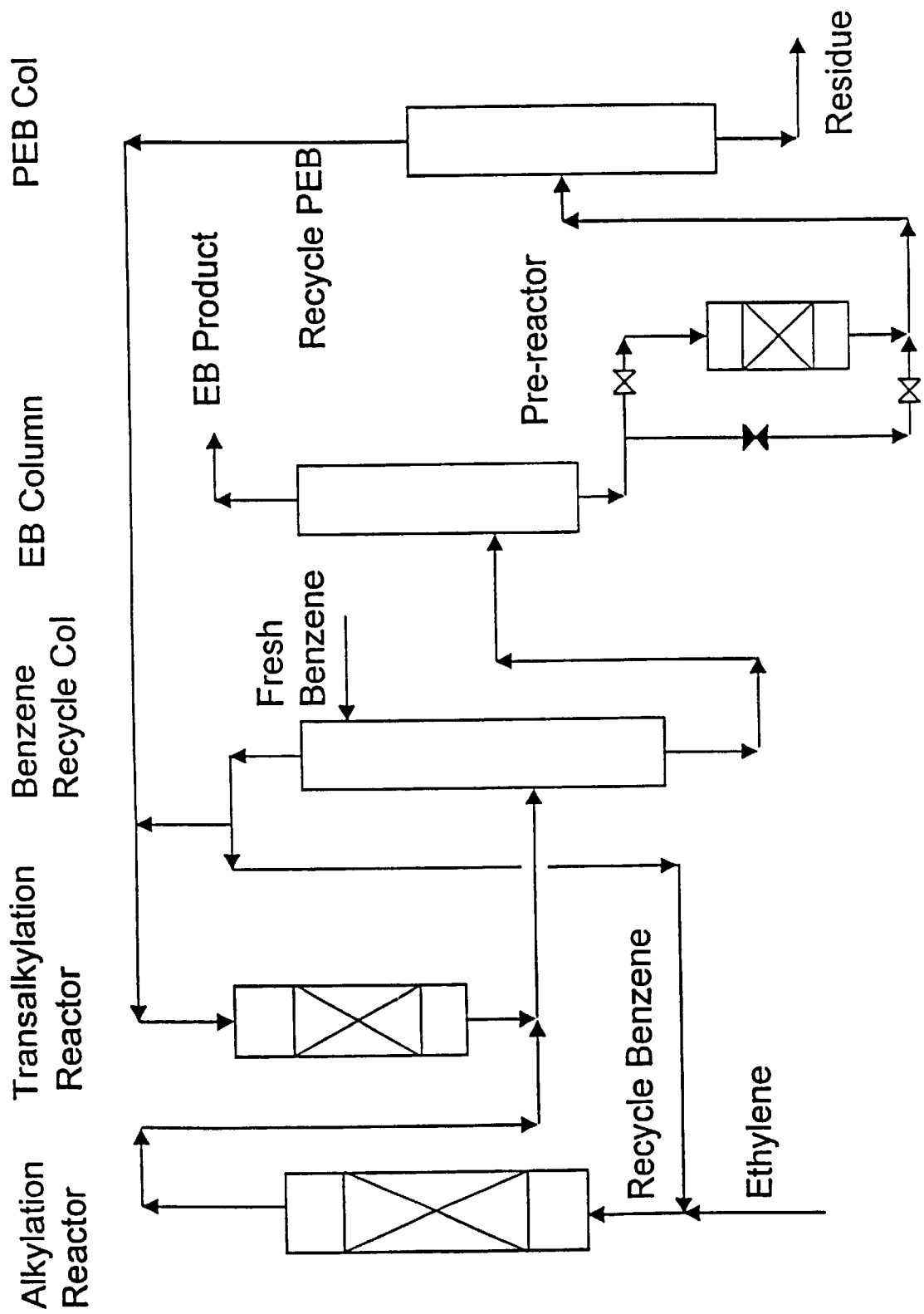

AROMATIC ALKYLATION PROCESS

FIELD OF THE INVENTION

This invention relates to a process for removing impurities from an alkylation process, and also relates to the improved alkylation process resulting therefrom.

BACKGROUND

In an aromatic alkylation process, alkylated aromatic compounds are prepared by alkylating an aromatic compound with an alkylating agent. The alkylation process is typically carried out in the presence of an acid which can be in the form of either a liquid or a solid. Examples of such acids include $AlCl_3$, $BF_3$, and zeolites. Zeolites are preferred in many instances because they eliminate problems associated with disposal and reclamation. The particular alkylated aromatic product that is desired is often a monoalkylated aromatic compound such as ethylbenzene or cumene (isopropyl benzene). Polyalkylated aromatic compounds may be formed in the process of manufacturing the monoalkylated product, and must be either removed or converted. Advantageously, there are transalkylation reactions that convert the polyalkylated aromatic to the desired monoalkylated aromatic compound. For example, in a process scheme to produce ethylbenzene, unwanted diethylbenzene produced in the alkylation step is converted to ethylbenzene in a transalkylation step. Thus, a transalkylation step is often an integrated part of a high yield alkylation process.

The polyalkylated aromatic feedstream to the transalkylation reactor may contain impurities such as aromatic or aliphatic olefins, aromatic or aliphatic diolefins, styrene, oxygenated organic compounds, sulfur containing compounds, nitrogen containing compounds such as collidine, oligomeric compounds such as polystyrene, and combinations thereof. Whereas vapor phase transalkylation processes are typically resistant to the presence of such impurities, liquid phase transalkylation processes are very susceptible to catalyst contamination, deactivation, plugging and the like by virtue of contact with any or all of these transalkylation feed contaminants. Many other factors favor liquid phase transalkylation units in an overall alkylation process scheme, and therefore a method and apparatus to effectively remove such contamination would be desirable.

Many methods and materials have been proposed for the removal of contaminants from hydrocarbon streams. U.S. Pat. No. 2,778,863 describes a multi-step clay treatment process for aromatics containing streams to overcome the clay fouling problems caused by diolefins in other clay treatment processes. Clays such as bentonite or synthetic alumina and/or silica-containing material are disclosed in U.S. Pat. No. 3,835,037 for use in a low temperature process for oligomerization/polymerization of color forming olefinic impurities in an aromatics stream such as a naphtha fraction. A process utilizing a silica alumina cracking catalyst in slurry form to contact and polymerize olefins and diolefins in a steam cracked naphtha stream is proposed in U.S. Pat. No. 3,400,169. The proponents of the process disclosed in U.S. Pat. No. 4,795,550 surveyed the aforementioned hydrocarbon purification processes and proposed the use a liquid phase process with a solid medium comprising a crystalline aluminosilicate zeolite such as faujasite and a refractory oxide to remove bromine-reactive olefinic impurities from aromatics containing streams. Co-pending, commonly assigned U.S. patent application Ser. No. 09/017,777, entitled "DECREASING BI REACTIVE CONTAMINANTS IN AROMATIC STREAMS", discloses a process wherein the aromatics stream is pre-treated to remove di-olefins prior to contact with the acid active catalyst material which removes mono-olefinic bromine reactive hydrocarbon contaminants.

Hydrocarbon separation processes utilizing the selective sorption properties of certain zeolite materials, including specially treated zeolite materials, have been proposed in U.S. Pat. Nos. 3,888,939 and 4,309,281. The removal of nitrogen containing compounds from a hydrocarbon stream by using a selective adsorbent, such as ZSM-5, having an average pore size less than about 5.5 Angstroms is disclosed in U.S. Pat. Nos. 5,744,686, 5,330,946 discloses a bentonite clay-based catalyst, suitable for removing olefins from aromatics streams, manufactured by adhering together a plurality of smaller acid-activated bentonite clay particles using a strong mineral acid as a binder. The use of spent catalysts for purification of aromatic streams by diolefin saturation and CCR removal at temperature low enough to reduce olefin polymerization reactions is proposed in U.S. Pat. No. 4,501,652.

It would be desirable to have a simple, single step process suitable for removing and/or converting most or all of the various different types of organic and inorganic contaminants which may be present in an alkylation/transalkylation process unit such that the valuable liquid phase transalkylation catalyst material will not be deactivated and/or plugged by these contaminants, thus reducing downtime and capital costs, while improving yields and material costs.

SUMMARY

There is provided an improved alkylation process embodying a process for purifying an aromatic alkylation process stream comprising providing an alkylated aromatic product comprising at least one alkyl group and at least one polyalkylated aromatic compound. At least a portion of this process stream comprising an alkylated aromatic product comprising at least one alkyl group and at least one polyalkylated aromatic compound is contacted with a purification medium in a liquid phase pre-reaction step to remove impurities and form a purified stream. The purified stream may then be further processed by liquid phase transalkylation to convert at least a portion of the at least one polyalkylated aromatic compound to a monoalkylated aromatic compound.

The purification medium is preferably a large pore molecular sieve catalyst selected from the group consisting of MCM-22, MCM-36, MCM-49, MCM-56, MCM-58, zeolite beta, faujasite, mordenite, and combinations thereof, although MCM-22, MCM-36, MCM-49, and MCM-56 are preferred. The purification medium may purify the alkylation stream, prior to transalkylation, by a combination of sorption and catalytic conversion.

BRIEF DESCRIPTION OF THE DRAWINGS

The accompanying drawing shows a process configuration in accordance with an embodiment of the invention.

DETAILED DESCRIPTION OF THE INVENTION

In the improved alkylation process of the invention, at least one alkylatable aromatic compound is contacted with at least one alkylating agent under sufficient reaction conditions and in the presence of a catalyst to provide an alkylated aromatic product comprising at least one alkyl group derived from said alkylating agent and at least one polyalkylated aromatic compound. Then at least a portion of said product is contacted with a purification medium in a liquid phase pre-reaction step to remove impurities and form a purified stream comprising said at least one polyalkylated aromatic compound. The purified stream and at least one alkylatable aromatic compound are then contacted under liquid phase conditions in a transalkylation section in the presence of a catalyst to convert at least a portion of said at least one polyalkylated aromatic compound to a monoalkylated aromatic compound.

Most aromatic alkylation processes having a liquid phase transalkylation step are suitable for the improvement in accordance with the process of the present invention by the addition of a purification step as described above. For example, U.S. Pat. Nos. 4,962,256; 4,992,606; 4,954,663; 5,001,295; and 5,043,501, each of which are incorporated herein by reference in their entirety for the purpose of describing particular alkylation processes, describe alkylation of aromatic compounds with various alkylating agents over catalyst comprising a particular crystalline material, such as PSH-3 or MCM-22. U.S. Pat. No. 4,962,256 describes preparing long chain alkylaromatic compounds by alkylating an aromatic compound with a long chain alkylating agent. U.S. Pat. No. 4,992,606 describes preparing short chain alkylaromatics by alkylating an aromatic compound with a short chain alkylating agent. U.S. Pat. No. 4,954,663 teaches alkylation of phenols, and U.S. Pat. No. 5,001,295 teaches alkylation of naphthalene. U.S. Pat. No. 5,043,501 describes preparation of 2,6-dimethylnaphthalene. These are a few examples, although certainly not an exhaustive listing, of the types of alkylation processes which may become improved alkylation processes in accordance with the present invention.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom (e.g., N or S) are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene.

Generally the alkyl groups which can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Typical aromatic alkylation reactions which may be improved by use of a step of contacting with the purification medium in accordance with the present invention include obtaining ethylbenzene from the reaction of benzene with ethylene, cumene from the reaction of benzene with propylene, ethyltoluene from the reaction of toluene with ethylene, and cymenes from the reaction of toluene with propylene.

The alkylated aromatic product stream obtained in the conventional aromatic alkylation processes described above may contain impurities such as, for example, olefins, diolefins, styrene, oxygenated organic compounds, sulfur containing compounds, nitrogen containing compounds, oligomeric compounds, and combinations thereof. These impurities or contaminants can deactivate or plug transalkylation catalyst. These impurities may originate from external feed streams or may be produced in either liquid or vapor phase alkylation reactors, or they may come from both of these sources.

In the process of the present invention these impurities are removed through adsorption and reaction in a treatment step carried out in a 'pre-reactor' which contains the purification medium. The removal of these impurities extends the cycle length of the transalkylation reactor by preventing poisoning and potential plugging of the valuable transalkylation catalyst. The operating conditions of the pre-reactor are such that the feed is in the liquid phase and at sufficient temperature to react the olefins, diolefins, and styrene and other highly reactive molecules to form heavy alkylaromatics.

In embodiments of the invention, the aromatic stream to be purified, i.e. containing some or all of the above-referenced impurities, is brought into contact with the purification medium in a suitable pre-reaction zone such as, for example, in a flow reactor containing a fixed bed comprising the purification medium composition, under effective liquid phase conditions to effect the removal of the impurities by reaction and/or adsorption. In the case of the oxygenates and sulfur compounds as well as in the case of heavier, oligomeric compounds such as polystyrene, in addition to converting some of these molecules to less reactive heavier molecules, the purification medium also acts as a sorbent bed. The conditions employed in the purification step include a temperature of from about 100° F. to about 600° F., and preferably between about 150° F. and 500° F., a weight hourly space velocity (WHSV) of between about 0.1 $hr^{-1}$ and about 200 $hr^{-1}$, and preferably from 0.5 $hr^{-1}$ to about 100 $hr^{-1}$, and a pressure between about ambient and 400 psig.

The purification medium may be a molecular sieve catalyst, preferably a large pore zeolite catalyst such as beta, MCM-22, MCM-36, MCM-49, MCM-56, MCM-58, faujasite, or mordenite. MCM-22, MCM-36, MCM-49, and MCM-56 are especially preferred.

The entire contents of U.S. Pat. No. 4,954,325, teaching MCM-22; U.S. Pat. No. 5,250,277, teaching MCM-36; U.S. Pat. No. 5,236,575, teaching MCM-49; and U.S. Pat. No. 5,362,697, teaching MCM-56 are incorporated herein by reference.

MCM-22, MCM-36, MCM-49, and MCM-56 are especially effective in removing both olefins and styrenes from heavy reformate and UDEX extract streams by reacting them to produce heavy alkylaromatics. Liquid phase operating conditions using MCM-22, MCM-36, MCM-49, and MCM-56 which are preferred for obtaining these results are 10–40 WHSV, 270–410° F. and 100 to 300 psig. Low MCM-22, MCM-36, MCM-49, and MCM-56 can also tenaciously adsorb nitrogen species such as collidine at the contemplated liquid phase conditions. Finally, alkylation studies have shown that olefins have little propensity to oligomerize over MCM-22, MCM-36, MCM-49, and MCM-56 under the contemplated liquid phase conditions. These three attributes of the molecular sieve purification medium of the invention: (1) high reactivity for alkylation, (2) strong retention of poisons such as basic nitrogen compounds, and (3) low reactivity for oligomerization, make MCM-22, MCM-36, MCM-49, or MCM-56 particularly preferred as a purification medium component for the improved alkylation process of the invention.

In embodiments of the invention where the purification medium is a molecular sieve catalyst, it may be desired to incorporate the purification medium with another material resistant to the temperatures and other conditions employed in the purification step. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst, however, in the present context of the invention active clay binders and the like may be used to improve the purification properties of the purification medium. Alternately, binders may be selected such that they do not participate in the removal of impurities, i.e., they are passive in the process of the invention.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the molecular sieve catalyst also include porous high surface area oxides such as silica, alumina, zirconia, titania or another include porous high surface area inorganic oxide.

In addition to the foregoing materials, the molecular sieve catalyst serving as a purification medium can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia, and silica-magnesia-zirconia.

The relative proportions of finely divided purification medium and inorganic oxide matrix vary widely, with the purification medium content ranging from about 1 to about 100 percent by weight and more usually, particularly when the composite is prepared in the form of beads, in the range of about 2 to about 90 weight percent of the composite.

Optionally, the molecular sieve purification medium may be tabletted or pelleted or otherwise produced in a shaped form so that no binder is present.

The molecular sieve purification medium can also contain a metal function such that unsaturated compounds are converted to saturated compounds in the presence of a hydrogen co-feed. For example, a hydrogenating component such as tungsten, vanadium, molybdenum, rhenium, nickel, cobalt, chromium, manganese, or a noble metal such as platinum or palladium may be used where a hydrogenation-dehydrogenation function is to be performed. Such component can be in the purification medium composition by way of co-crystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal- containing ion. Thus, suitable platinum compounds for this purpose include chloroplatinic acid, platinous chloride and various compounds containing the platinum amine complex.

The improved alkylation process described herein, specifically the pre-reaction step carried out in the presence of a purification medium, can be carried out as a batch-type, semi-continuous or continuous operation utilizing a fixed or moving bed catalyst system. In embodiments of the invention, two pre-reactors may be situated in parallel, so that they can be operated in a swing mode. The location of the pre-reactor can be located directly up-stream of the transalklyator or in the distillation section as shown in the accompanying drawing. The drawing is a sketch of the particular process scheme for the improved alkylation process of the invention for a liquid phase ethylbenzene unit wherein the pre-reactor is located downstream of the ethylbenzene column and upstream of the PEB (polyethylbenzene) column. The pre-reactor as shown here is designed to be bypassed when the catalyst is spent or if polymer formation causes excess pressure drop. The location of the pre-reactor in the distillation section of the improved alkylation process of the invention can be changed depending on the impurity to be removed. If the major impurities to be removed are reactive olefins such as styrene, the pre-reactor can be located upstream of the ethylbenzene column with hydrogen co-feed to convert the unsaturated molecules to the saturated version thereof For example, styrene would be converted to ethylbenzene. In the improved alkylation process of the invention, the pre-reactor can be used upstream of any transalkylation process, including cumene and other higher alkyl aromatic production processes described above.

In order to preclude plugging of the catalyst bed, the bed optionally may be 'graded' by structuring the bed so that larger catalyst particles are placed at the entrance to the bed. In this manner, the interstitial volume between the particles is larger at the entrance, for example the top of the bed, thereby allowing a greater amount of contaminant residue to build up on the catalyst before the bed begins to constrict flow. This will have the effect of extending the life of the bed.

In the process of the invention, the purified stream is contacted under liquid phase conditions in a transalkylation section in the presence of a catalyst to convert at least a portion of the at least one polyalkylated aromatic compound to a monoalkylated aromatic compound. It is generally known to improve the yield of monoalkylated product by producing additional monoalkylated product by transalkylation. The polyalkylated products may be recycled to the alkylation reactor to undergo transalkylation or they may be reacted with additional aromatic feed in a separate reactor. It may be preferred to blend the bottoms from the distillation of monoalkylated product with a stoichiometric excess of the aromatic feed, and react the mixture in a separate reactor over a suitable transalkylation catalyst. The transalkylation catalyst may be a catalyst comprising a zeolite such as MCM-49, MCM-22, MCM-56, PSH-3, SSZ-25, zeolite X, zeolite Y, zeolite beta, or mordenite. Such transalkylation reactions over zeolite beta are disclosed in the U.S. Pat. No. 4,891,458; and further such transalkylations using an acid dealuminized mordenite are disclosed in U.S. Pat. No. 5,243,116. The effluent from the transalkylation reactor is blended with alkylation reactor effluent and the combined stream distilled. A bleed may be taken from the polyalkyated product stream to remove unreactive heavies from the loop or the polyalkylated product stream may be distilled to remove heavies prior to transalkylation.

The invention and pre-reactor are of particular value where the vapor phase alkylation unit uses "dirty" feedstocks such as dilute ethylene sourced from FCC off gas. Polyethylbenzene (PEB) from such alkylation units is likely to be contaminated with impurities, such as those cited above which may cause deactivation and/or plugging of the liquid phase transalkylation reactor.

The process of the invention allows a revamp of older alkylation process units with a liquid phase transalkylator at a significantly lower capital cost. Use of liquid phase transalkylator instead of a vapor phase transalkylator will also produce significantly higher product purity, specifically xylene impurities in the case of ethylbenzene production. Capacity expansion is achieved by incorporation of liquid phase transalkylator at facilities that did not previously have transalkylation capability and makes it possible to debottleneck the alkylation unit. The present invention may obtain incremental improvement in the overall yield and feedstock utilization efficiency. The present invention may also be used in units where, for what ever reason, the PEB has a high level of olefins and styrene or other impurities that can deactivate transalkylation catalysts.

What is claimed is:

1. An aromatic alkylation process comprising:
    contacting at least one alkylatable aromatic compound with at least one alkylating agent under sufficient reaction conditions and in the presence of a catalyst to provide an alkylated aromatic product comprising at least one monoalkylated aromatic compound and at least one polyalkylated aromatic compound; and
    contacting at least a portion of said product with a purification medium comprising a molecular sieve catalyst selected from MCM-22, MCM-36, MCM-49, MCM-56 and combinations thereof in a liquid phase pre-reaction step to remove impurities and form a purified stream comprising said at least one polyalkylated aromatic compound; and
    contacting said purified stream with at least one alkylatable aromatic compound under liquid phase conditions in a transalkylation section in the presence of a catalyst to convert at least a portion of said at least one polyalkylated aromatic compound to a monoalkylated aromatic compound.

2. The process of claim 1 wherein said impurities are selected from the group consisting of olefins, diolefins, styrene, oxygenated organic compounds, sulfur containing compounds, nitrogen containing compounds, oligomeric compounds, and combinations thereof.

3. The process of claim 1 wherein said purification medium comprises particles and has a greater interstitial volume between said particles at an upstream portion, compared to an interstitial volume of a downstream portion of said purification medium.

4. The process of claim 1 wherein said purification medium is contained in a pre-reactor located directly upstream of said transalkylation section.

5. The process of claim 1 wherein said purification medium is contained in a pre-reactor located in a distillation section of said alkylation process.

6. The process of claim 1 wherein said alkylatable aromatic compound is benzene and said alkylating agent is ethylene or propylene.

7. The process of claim 1 wherein said purification medium further comprises a metal function such that unsaturated compounds are converted to saturated compounds in the presence of a hydrogen co-feed.

8. An aromatic alkylation process comprising the steps of:
    (a) contacting at least one alkylatable aromatic compound with at least one alkylating agent in the presence of a catalyst to provide an alkylation product comprising at least one monoalkylated aromatic compound and at least one polyalkylated aromatic compound;
    (b) contacting at least a portion of the alkylation product with a purification medium comprising a molecular sieve catalyst selected from MCM-22, MCM-36, MCM-49, MCM-56 and combinations thereof in a liquid phase pre-reaction step to remove impurities and form a purified stream comprising at least one polyalkylated aromatic compound;
    (c) before or after step (b), separating said at least one monoalkylated aromatic compound from the alkylation product; and
    (d) after steps (b) and (c), contacting the purified stream with at least one alkylatable aromatic compound under liquid phase conditions in a transalkylation section in the presence of a catalyst to convert at least a portion of said at least one polyalkylated aromatic compound to a monoalkylated aromatic compound.

9. An aromatic alkylation process comprising:
    contacting at least one alkylatable aromatic compound with at least one alkylating agent under sufficient reaction conditions and in the presence of a catalyst to provide an alkylated aromatic product comprising at least one monoalkylated aromatic compound and at least one polyalkylated aromatic compound; and
    contacting at least a portion of said product with a purification medium comprising MCM-22 in a liquid phase pre-reaction step to remove impurities and form a purified stream comprising said at least one polyalkylated aromatic compound; and contacting said purified stream with at least one alkylatable aromatic compound under liquid phase conditions in a transalkylation section in the presence of a catalyst to convert at least a portion of said at least one polyalkylated aromatic compound to a monoalkylated aromatic compound.

* * * * *

UNITED STATES PATENT AND TRADEMARK OFFICE
CERTIFICATE OF CORRECTION

PATENT NO. : 6,313,362 B1
DATED : November 6, 2001
INVENTOR(S) : John R. Green, Thomas F. Degnan, Yun-Yang Huang, Chaya R. Venkat, and Ronald A. Weiss It is certified that error appears in the above-identified patent and that said Letters Patent is hereby corrected as shown below:

<u>Title page,</u>
Assignee, please delete "ExxonMobil Corporation" and insert therefore,
-- ExxonMobil Oil Corporation --.

Signed and Sealed this

Second Day of April, 2002

Attest:

JAMES E. ROGAN
Attesting Officer
Director of the United States Patent and Trademark Office